United States Patent
Butler

(10) Patent No.: US 8,562,655 B2
(45) Date of Patent: Oct. 22, 2013

(54) BONE PLATE ASSEMBLY

(75) Inventor: Charles L. Butler, Rancho Cucamonga, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 592 days.

(21) Appl. No.: 12/460,390

(22) Filed: Jul. 17, 2009

(65) Prior Publication Data
US 2010/0042159 A1 Feb. 18, 2010

Related U.S. Application Data

(60) Provisional application No. 61/135,360, filed on Jul. 17, 2008.

(51) Int. Cl.
*A61B 17/80* (2006.01)
(52) U.S. Cl.
USPC .......................................... 606/289; 606/286
(58) Field of Classification Search
USPC ................. 606/288–291, 293–295, 302, 303; 623/17.11–17.16
See application file for complete search history.

(56) References Cited

U.S. PATENT DOCUMENTS

| | | | | |
|---|---|---|---|---|
| 6,361,537 | B1 * | 3/2002 | Anderson | 606/86 B |
| 6,413,259 | B1 * | 7/2002 | Lyons et al. | 606/295 |
| 6,740,088 | B1 * | 5/2004 | Kozak et al. | 606/286 |
| 2005/0075633 | A1 * | 4/2005 | Ross | 606/61 |
| 2006/0149253 | A1 * | 7/2006 | Doubler et al. | 606/69 |
| 2006/0229618 | A1 * | 10/2006 | Dube | 606/69 |
| 2007/0213728 | A1 * | 9/2007 | Lindemann et al. | 606/69 |

* cited by examiner

*Primary Examiner* — Nicholas Woodall
(74) *Attorney, Agent, or Firm* — Michael J. Loi

(57) ABSTRACT

A lumbar plate assembly for use between at least two vertebral bodies is disclosed. The assembly includes a lumbar plate having at least one opening for each vertebral body, a screw configured to secure the lumbar plate to a vertebra through the at least one opening, and a rotatable locking mechanism proximate the least one opening configured to rotate from a first configuration to a second configuration, the first configuration allowing the screw to pass into the opening and the second configuration engaging the screw to prevent withdrawal of the screw from the opening.

14 Claims, 6 Drawing Sheets

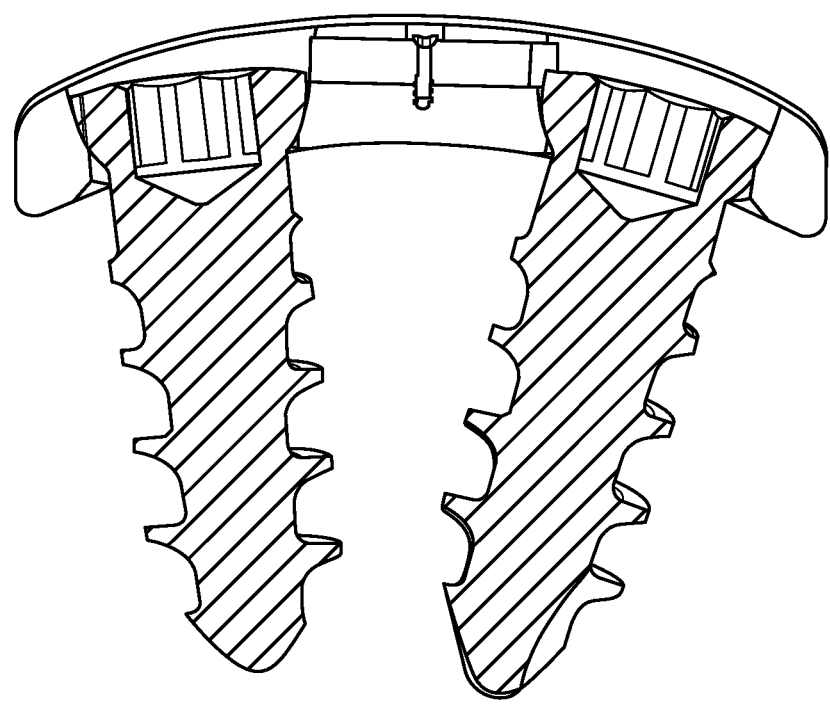
FIG. 7
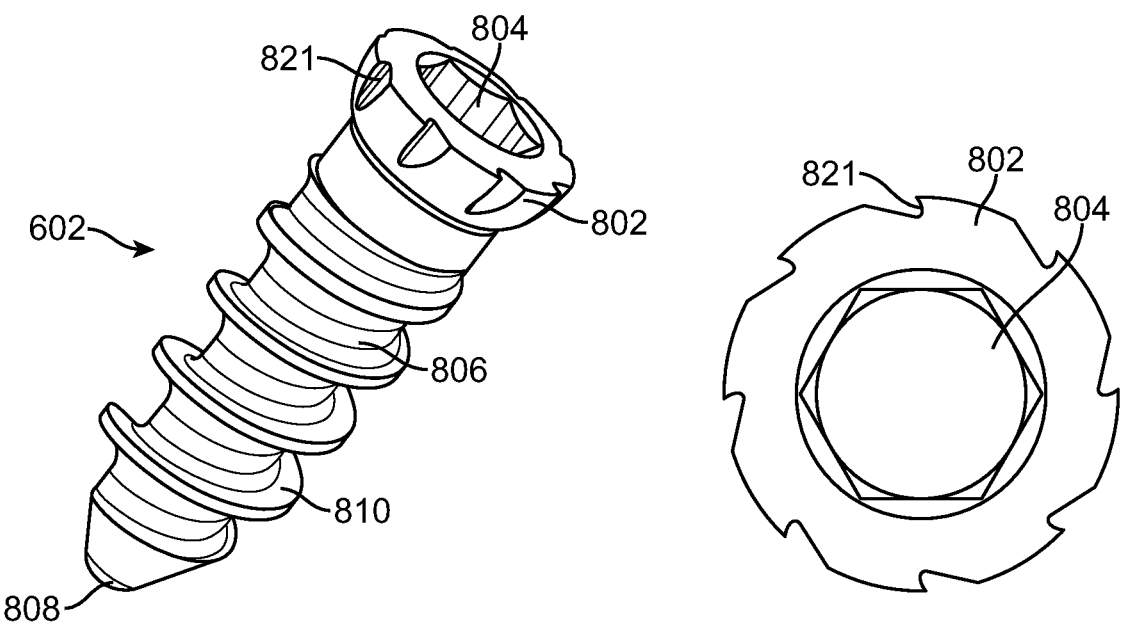
FIG. 8
FIG. 9

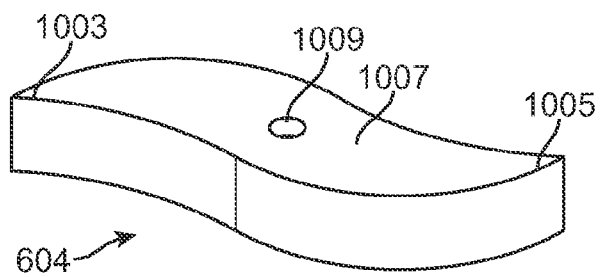
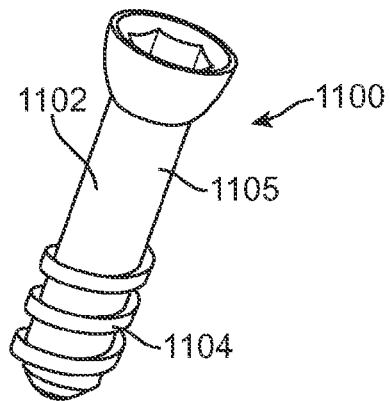
FIG. 10     FIG. 11
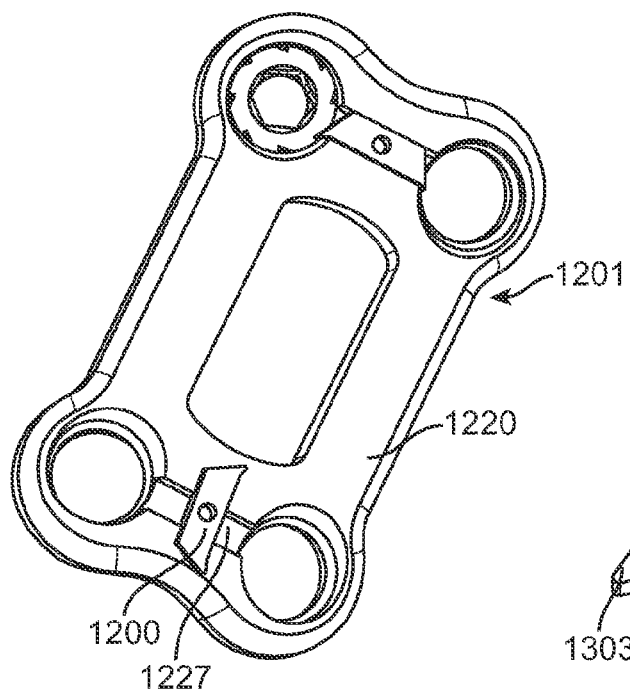
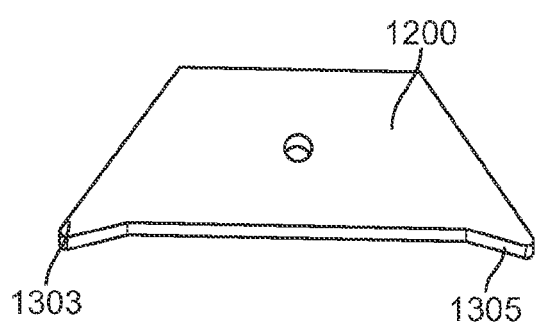
FIG. 12     FIG. 13

BONE PLATE ASSEMBLY

CROSS-REFERENCES TO RELATED APPLICATIONS

The present application claims priority to U.S. Provisional Patent Application No. 61/135,360 to Butler, filed Jul. 17, 2008, and entitled "A BONE PLATE ASSEMBLY", the disclosure of which is incorporated herein by reference in its entirety.

BACKGROUND OF THE INVENTION

1. Field of the Invention

The present invention generally relates to the field of spinal surgery. In particular, the present invention relates to the field of surgical access to the spine. More particularly, the present invention relates to an apparatus for internal fixation of the spine and a novel locking mechanism for a bone plate assembly.

2. Background

An increasingly accepted procedure for treating spinal disorders involves using substantially rigid plates to hold vertebrae in desired spatial relationships and orientations relative to each other. The upper cervical spine can be approached anteriorly or posteriorly, although anterior approaches are of more interest in connection with this invention. In either case, holes are drilled and tapped in at least two of the vertebrae, to receive screws or other fasteners used to secure the plate. The holes are accurately positioned with reference to openings formed through the cervical plate. In some cases the screws may be self-tapping. Typically the plate is curved about its longitudinal axis to facilitate contiguous surface engagement of the plates with the vertebrae. With the plate maintained against the vertebrae, the fasteners are secure within the holes. As a result, the plate maintains the attached vertebrae in a desired spacing and orientation with respect to each other.

One of the problems associated with this technique is the tendency of screws or other fasteners to gradually work loose after fixation. Slight shock or vibration of the vertebrae, due to walking, climbing stairs or more vigorous activity by the patient following treatment increases this tendency, jeopardizing the integrity of fixation. Moreover, as the fasteners work loose, the outward protrusion of the heads over other components of the fasteners can be a source of discomfort and present the risk of trauma to adjacent and surrounding soft tissue.

The curvature of cervical plates typically results in a convergence of fasteners that extend through spaced apart openings in the plate, particularly when each screw is perpendicular to the region of the plate surrounding it. Screws sufficiently short to avoid interfering with one another may not be long enough to assure a secure plate fixation. Further, the physician may encounter difficulties in positioning the plate if one of the vertebrae, due to a particular shape and orientation, cannot readily retain a perpendicularly inserted fastener.

There remains a need for greater flexibility in positioning and orienting the bone screws or fasteners, and for a simpler, more reliable means of counteracting the tendency of the bone screws to work loose after cervical plate fixation.

Therefore, it is an object of the present invention to provide a bone plate and fixation system in which bone screws or other fasteners are more securely retained and less likely to work loose, without the need for auxiliary screws or other additional fixtures

SUMMARY OF THE INVENTION

Generally, embodiments of the present invention provide a lumbar plate locking assembly. The assembly includes a lumbar plate having at least one opening, a screw configured to be secured to the lumbar plate through the at least one opening, and a locking mechanism disposed at the least one opening and configured to lock the screw to the lumbar plate to prevent the screw from unintentionally backing out, reversing out, or falling out from the opening. Upon rotation of the locking mechanism in one direction or first configuration, the screw is locked to the lumbar plate and upon rotation of the locking mechanism in another direction or second configuration, the screw is unlocked.

In a first aspect, embodiments of the present invention provide a lumbar plate assembly for use between at least two vertebral bodies including a lumbar plate having at least one opening for each vertebral body, a screw configured to secure the lumbar plate to a vertebra through the at least one opening, and a rotatable locking mechanism proximate the least one opening configured to rotate from an first configuration to a second configuration, the first configuration allowing the screw to pass into the opening and the second configuration engaging the screw to prevent withdrawal of the screw from the opening.

In many embodiments, the system further includes a locking screw configured to secure the locking mechanism to the plate.

In many embodiments, the lumbar plate includes a recessed portion configured to accommodate placement of the locking mechanism.

In many embodiments, the locking mechanism includes a center portion and at least protrusion coupled to the center portion, and the at least one protrusion is further configured to engage a partially covered channel within the recessed portion.

In many embodiments, the at least one protrusion is configured to protrude into the at least one opening and engage the screw upon rotating the locking mechanism to the second configuration.

In many embodiments, the screw includes at least one notch disposed on a top portion of the screw and the locking mechanism includes a portion configured to interact with the at least one notch of the screw upon rotating the locking mechanism to the second configuration.

In many embodiments, the locking mechanism includes at least one smooth surface configured to create a substantially uninterrupted surface with an interior surface of the at least one opening in the first configuration.

In many embodiments, the locking mechanism is configured to have a trapezoidal shape and include at least one locking hook for engaging the screw.

In many embodiments, the lumbar plate includes two screw openings configured to accommodate placement of two screws. In many embodiments, the locking mechanism is configured to be positioned between the two openings and further configured to simultaneously secure at least two screws within the two openings upon rotating the locking mechanism to the second configuration.

In another aspect, embodiments of the present invention provide a lumbar plate locking assembly including a lumbar plate having at least one opening, a screw configured to be secured to the lumbar plate through the at least one opening, and a locking mechanism disposed at the least one opening and configured engage the screw to prevent the screw from withdrawing from the opening, wherein upon rotation of the locking mechanism in one direction, the screw is locked to the lumbar plate and upon rotation of the locking mechanism in another direction, the screw is unlocked.

In many embodiments, the lumbar plate includes a recessed portion configured to accommodate placement of the rotatable locking mechanism. In many embodiments, the locking mechanism is rotatably secured within the recessed portion. In many embodiments, the system further includes a locking screw configured to secure the locking mechanism within the recessed portion. In many embodiments, the recessed portion includes at least one channel configured to connect the recessed portion and the at least one opening, wherein the at least one channel is configured to be partially covered, thereby creating a locking arrangement between the locking mechanism and the lumbar plate. In many embodiments, the at least one channel includes at least one uncovered portion through which the locking mechanism is inserted into the recessed portion. In many embodiments, the locking mechanism includes a center portion and at least protrusion coupled to the center portion, and the at least one protrusion is further configured to fit within the at least one channel. In many embodiments, the at least one protrusion is configured to protrude into the at least one opening upon rotating the locking mechanism. In many embodiments, the at least one protrusion is further configured to engage the screw inserted into the at least one opening.

In many embodiments, the screw includes at least one notch disposed on a top portion of the screw and the locking mechanism includes at least one locking tip configured to interact with the at least one notch of the screw. In many embodiments, the locking mechanism includes at least one smooth surface configured to create a substantially uninterrupted surface with an interior surface of the at least one opening upon the locking mechanism being secured with the recessed portion in an unlocked state.

In many embodiments, the locking mechanism is configured to have a trapezoidal shape and include at least one locking hook for locking the screw.

In many embodiments, the lumbar plate includes four screw openings configured to accommodate placement of four screws. In many embodiments, the locking mechanism is configured to be disposed within a recessed portion between two openings of the four screw openings and further configured to simultaneously secure at least two screws of the four screws.

In many embodiments, the lumbar plate is configured to secure screws having a diameter in the range of 5.0 mm to 8.0 mm.

In another aspect, embodiments of the present invention provide a method of using a lumbar plate assembly between at least two vertebral bodies, the method including providing a lumbar plate having at least one opening at each vertebral body, inserting a screw through at least one opening, securing the lumbar plate to the vertebra with a screw through the at least one opening at each vertebral body, and rotating at least one locking mechanism proximate the at least one opening from a first configuration to a second configuration, the first configuration allowing the screw to pass into the opening and the second configuration engaging the screw to prevent withdrawal of the screw from the opening.

In many embodiments, the screw includes at least one notch disposed on a top portion of the screw and the locking mechanism includes a portion configured to interact with the at least one notch of the screw to prevent screw rotation in at least one direction.

In some embodiments, the present invention relates to a method of assembling a lumbar plate assembly. The assembly includes a lumbar plate having at least one opening, a screw configured to be secured to the lumbar plate through the at least one opening, and a locking mechanism disposed at the least one opening and configured to lock the screw to the lumbar plate to prevent the screw from falling out from the opening. The method includes steps of inserting the screw into the at least one opening, and rotating the locking mechanism in one direction to lock the screw.

BRIEF DESCRIPTION OF THE DRAWINGS

The present invention is described with reference to the accompanying drawings. In the drawings, like reference numbers indicate identical or functionally similar elements.

FIGS. 6-13 illustrate another exemplary anterior lumbar plate along with its various components, according to some embodiments of the present invention.

DETAILED DESCRIPTION OF THE INVENTION

FIGS. 1-5 illustrate an exemplary anterior lumbar plate 100 along with its various components, according to some embodiments of the present invention. In some embodiments, the lumbar plate 100 is an anterior stabilization plate that utilizes two bone screws per vertebral body (not shown in FIG. 1). While two bone screws per body are shown, other embodiments may include one screw or more than two screws per body. The lumbar plate 100 allows bone screw angulation to be convergent along a sagittal plane and divergent along an axial plane for maximum purchase and resistance to screw pullout. The lumbar plate includes a locking mechanism 103 (a, b), which is configured to secure bone screws 102(a, b, c, d) and prevent screw back-out. The lumbar plate 100 is further configured to restrict or block the bone screw from backing out of its tightened position.

Figure 1:
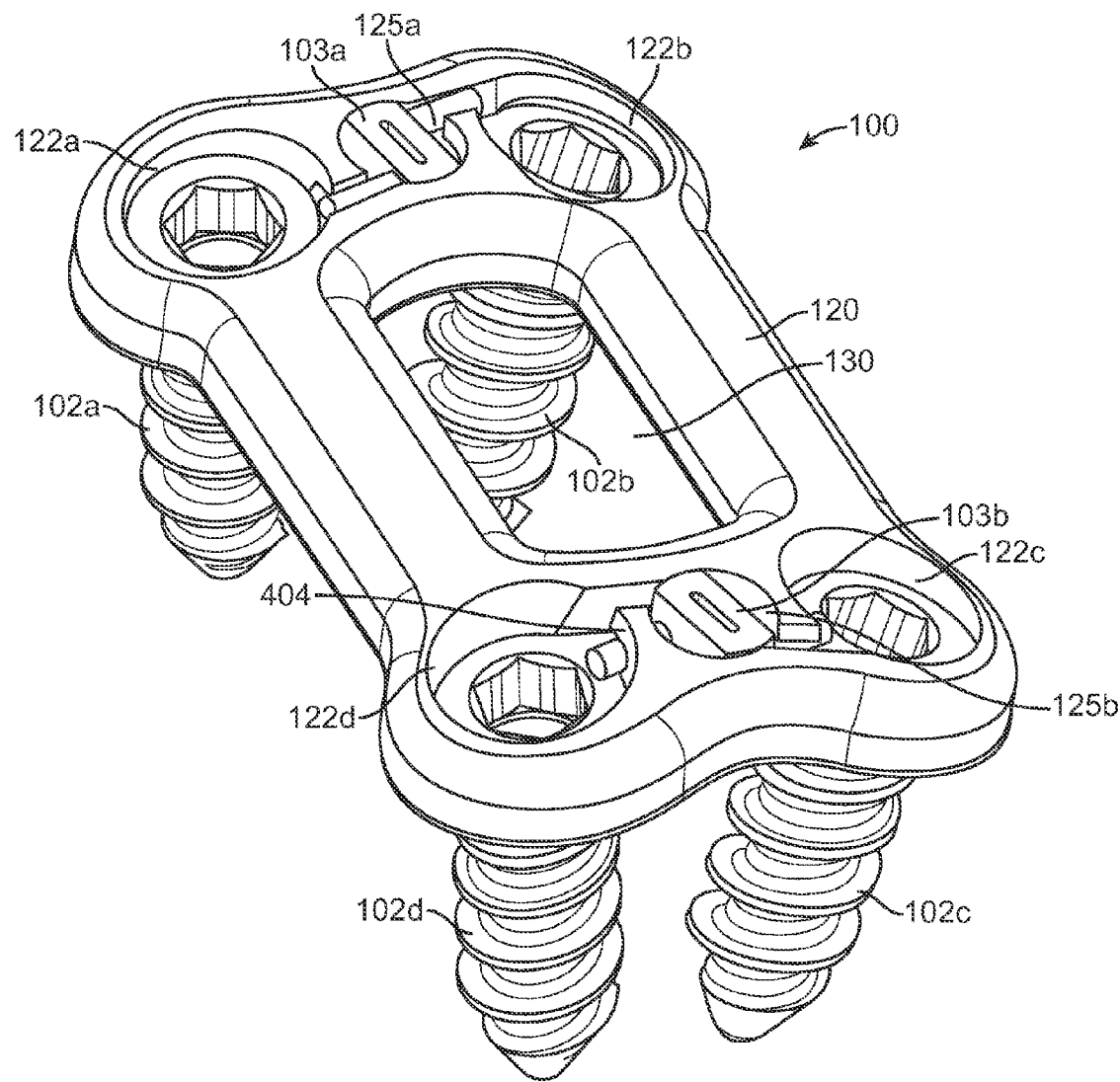
FIGS. 1-5 illustrate an exemplary anterior lumbar plate along with its various components, according to some embodiments of the present invention.

Referring to FIG. 1, the lumbar plate 100 includes a housing 120 having an interior opening 130 and screw openings 122(a, b, c, d) disposed about the opening 130, in the embodiment shown, the screw openings 122 are disposed symmetrically about the opening 130. In some embodiments, the lumbar plate 100 can include a plurality of interior openings or no interior openings at all. The screw openings 122 are configured to receive respective screws 102(a, b, c, d). In some embodiments, the lumbar plate 100 can accommodate placement of more than four screws (as illustrated in FIG. 1), or less than four screws (not shown). Further, the screws 102 can have various lengths, widths, shapes, or any other characteristics.

In some embodiments, the shape of the housing 120 of the lumbar plate 100 can be rectangular, whereby the screw openings 122 are configured to protrude away from the housing 120, as shown in FIG. 1. In some embodiments, the shape of the housing 120 can be square, circular, oval, polygonal, or any other desired shape. Further, the housing 120 has an arcuate shape, wherein, upon insertion of the screws 102, axis of the screws 102 are configured to converge toward each other (for example, the axis of the screw 102a is configured to be convergent with the axis of the screw 102b; similarly for screws 102c and 102d). In some embodiments, the axis of all or some of the screws 102 are configured to converge toward each other, upon being inserted into the screw openings 122. Such arrangement allows angular placement of the lumbar plate 100 on a vertebral body or any other bone in the body. As can be understood by one skilled in the art, the arcuation of the housing 120 of the lumbar plate 100 can have any angle (including 0 degrees (or 180 degrees), which would correspond to a flat lumbar plate 100). In some embodiments, the axis of all or some of the screws 102 are configured to be parallel or converge away each other. In some embodiments, the screw openings 122 can be configured to be contained within the housing 120 and not protrude away from its outer perimeter.

The screw openings 122 can be configured to retain screws 102 in various ways. In some embodiments, the screw openings 122 are configured to have a larger diameter near their top surface and a smaller diameter near their bottom surface. The smaller diameter can be selected to prevent screw 102 from falling through the opening 122 upon insertion of the screw 102. Hence, the smaller diameter can be smaller than the head portion of the screw 102. In some embodiments, the screw openings 122 can include screw retaining ledges (not shown) that are configured to protrude toward the center of the screw opening 122 and thereby, create a smaller diameter opening disposed in the screw opening 122. Such smaller diameter opening prevents screw 102 from falling through the opening 122 upon insertion. As can be understood by one skilled in the art, there are other ways of preventing screws 102 from falling through the openings 122. As can be understood by one skilled in the art, the openings 122 can have any desired shape, e.g., round, square, rectangular, polygonal, etc.

Figure 2:
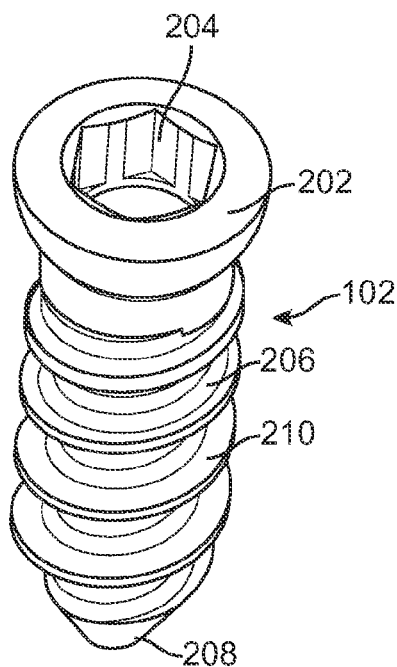

An exemplary screw 102 is illustrated in FIG. 2. Referring to FIG. 2, the screw 102 includes a top portion 202, a middle portion 210, and a tip portion 208. To place the screw into a bone, a user (or any medical professional) would place the tip portion 208 proximate to the bone, and upon application of an instrument to the top portion 202 exert an appropriate amount of force to drive (by rotating) the screw 102 into the bone. In some embodiments, the screw 102 is configured to be inserted into a pre-tapped hole in the bone. The middle portion 210 includes threading 206 that is configured to allow such driving in a circular motion. The top portion 202 further includes instrument retaining opening 204 that accommodates placement of tools and instruments for driving the screw into the bone. In some embodiments, the opening 204 can have a hexagonal arrangement that allows placement of specialized tooling that matches such arrangement. The top portion 202 of the screw 102 can have a smooth outside surface or, in the alternative, can have locking grooves, as shown in FIGS. 8 and 9 and discussed below.

Figure 3:
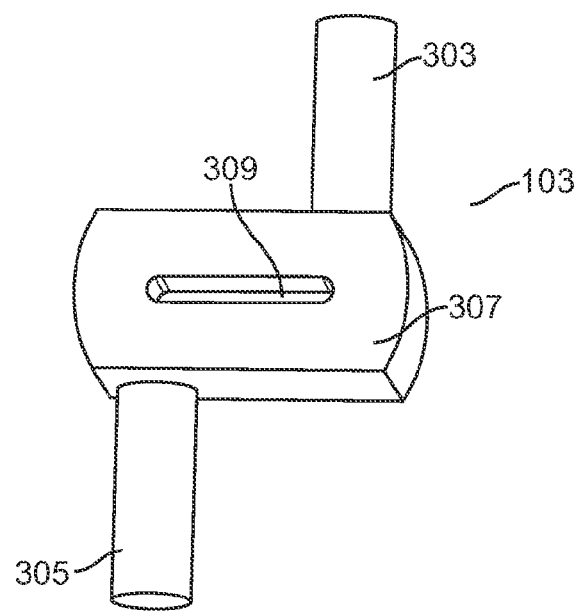
Figure 4:
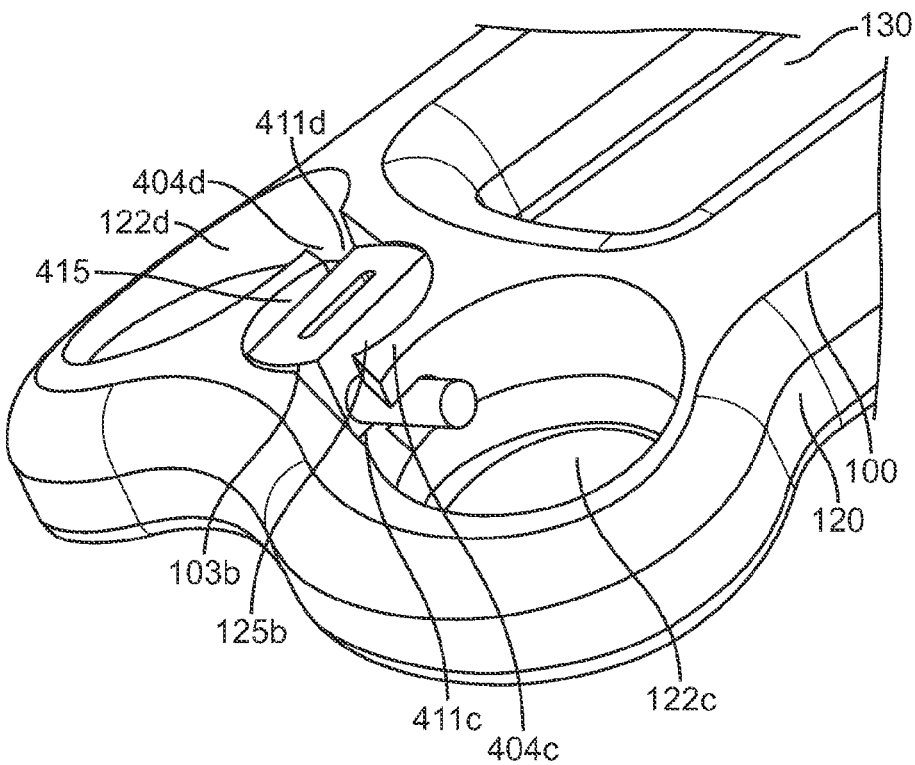

The housing 120 of the lumbar plate 100 further includes locking mechanisms 103(a, b). The locking mechanisms 103 are configured to be placed between screw openings 122 into their respective locking mechanism openings 125(a, b). The locking mechanism openings 125 are configured to connect screw openings 122. In some embodiments, the opening 125a is configured to connect screw openings 122a and 122b, and the opening 125b is configured to connect screw openings 122c and 122d. Referring to FIGS. 3 and 4, the locking mechanism 103 is illustrated (FIG. 3) being placed into the opening 125b. Referring to FIG. 4, the opening 125b is configured to include a center portion 415 connected to channels 411(c, d) on each side of the center portion 415. The channels 411 further connect with respective openings 122(c, d). The center portion 415 has a circular form that allows the locking mechanism 103b to rotate, once the mechanism 103b is placed into the center portion 415. The channels 411 are configured to be partially covered by respective extensions 404(c, d). The extensions 404 are configured to protrude from the body 120 of the lumbar plate 100. The extensions 404 further prevent the locking mechanism 103 from falling out, once it is secured inside the body 120.

Referring to FIG. 3, the locking mechanism 103 is illustrated in further detail. The mechanism includes a body portion 307 coupled to two protrusions 303, 305 on the body. In the embodiment shown, the protrusions are bars 303 and 305 on each side of the body 307. In some embodiments, the body portion 307 includes a slot 309 that allows detachable coupling of an instrument for rotation of the locking mechanism 103. In some embodiments, the body portion 307 includes rounded edge that allows the mechanism 103 to rotate inside the opening 125 (not shown in FIG. 3). Further, in some embodiments, the bars 303 and 305 can be configured to have a round cross-section that allows rotation of the bars inside the partially covered channels 411. As can be understood by one skilled in the art, the body 307 and the protrusion or bars 303, 305 can have any other desired shape. In some embodiments, the channels 411 and extensions 404 may have a locking feature to engage the protrusion or bars 303, 305 that locks the locking mechanism 103 in place when protrusion or bars 303, 305 lock the screw 102. This may include ramps or detents within channels 411 that engage protrusion or bars 303, 305. In other words, in this embodiment there may be two locking features, the first locking feature being when the protrusion or bars 303, 305 lock the screw 102 in the plate and the second locking feature being when the protrusion or bars 303, 305 are locked in the channels 411, so the locking mechanism does not rotated backwards to allow release of the screw.

Figure 5:
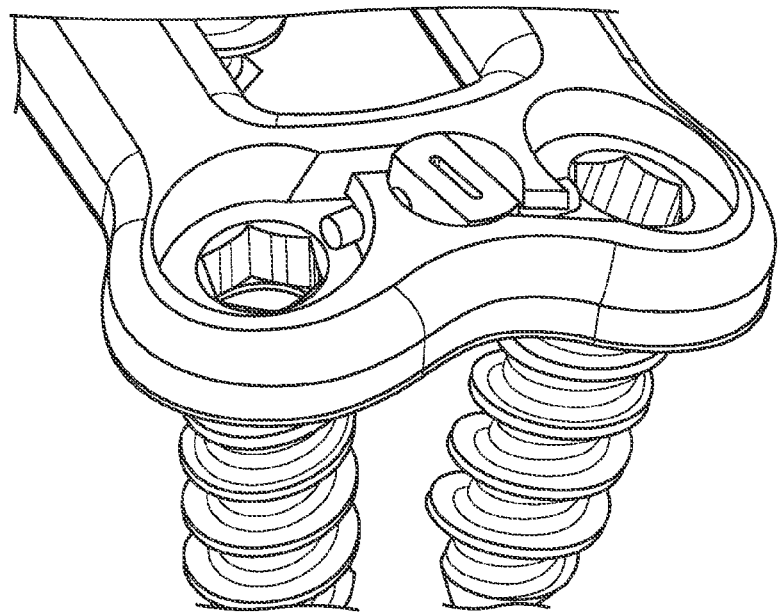

In one embodiment shown in FIG. 4, the locking mechanism 103 is placed into the opening 125 by aligning the bars 303, 305 with the channels 411 and dropping the mechanism 103 into the opening 125. The mechanism 103 is secured to the body 120 of the lumbar plate 100 after at least one screw 102 is placed into the screw openings 122 (as shown in FIG. 5). Once the screw 102 is inserted through the screw openings 122, the locking mechanism 103 is inserted into the opening 125 (with bars 303 and 305 being placed through the channels 411). To secure the screws 102, the locking mechanism 103 is rotated with the bars 303, 305 being rotated toward the partially closed portion of the channels 411. Hence, the bars 303, 305 lock the screws 102 to the screw openings 122, thereby preventing screws 102 from falling out. To unlock the screws 102, the locking mechanism 103 is rotated in an opposite direction and removed from the opening 125, thereby releasing the screws 102 and allowing them to be removed. As stated above, the rotation of the locking mechanism 103 can be accomplished using any number of tools (including hands). A locked lumbar plate 100 arrangement is illustrated in FIG. 5. In other embodiments, the locking mechanism 103 may be held in place within the opening 125 with a locking screw, such as screw 605 or 1100, discussed below. Once in place, the locking mechanism 103 may be rotated from a first position in which the bars 303, 305 are positioned to allow screws 102 be inserted through the screw openings 122 to a second position in which the bars 303, 305 engage and lock the screws 102 (shown in FIGS. 1 and 5).

FIGS. 6-13 illustrate another exemplary embodiment of an anterior lumbar plate 600, according to some embodiments of the present invention. FIG. 7 is a partial cross-sectional view of the assembled bone plate 600 along with screws 602(a, b, c, d). FIGS. 8-9 illustrate an exemplary bone screw 602 having a notched head (FIG. 9). FIG. 10 illustrates an exemplary curved locking tooth 604 shown in FIG. 6, according to some embodiments of the present invention. FIG. 11 illustrates an exemplary securing screw 1100 for securing the curved locking tooth 604, according to some embodiments of the present invention. FIGS. 12-13 illustrate another exemplary embodiment of the locking tooth 1200 for locking the screws 602. In some embodiments, the bone screws 602 can be have a diameter between 5.0 mm and 8.0 mm, preferable between 6.0 mm and 7.0 mm, and a length between 20 mm and 60 mm.

In some embodiments, the lumbar plate 600 is configured to allow unrestricted clockwise rotation of the bone screw 602 while restricting its counterclockwise rotation. The lumbar plate 600 includes an anti-counterclockwise rotation mechanism that is configured to allow the bone screw 602 to properly align with the stabilization plate 600 and be fully seated.

Referring to FIG. 8, bone screws are machined with "hook" shape notches in a circular pattern around the top face of the head (as shown in FIG. 9). A rectangular shaped recess 1227 is cut out of the bone plate 1220 horizontally between the two bone screw holes (as shown in FIG. 12). A threaded small diameter hole is drilled in the recess, centered horizontally and vertically between the bone screw holes. Once the bone screw is tightened, a trapezoidal shaped tooth (as shown in FIG. 13) is placed in the corresponding recess and secured to the plate with a small hex screw (as shown in FIG. 11). The curvature of the tooth lock into the "hook" notch in the bone screws and prevent the bone screw from rotating counter-clockwise or backing out. After further analysis, it was observed that the trapezoidal shape tooth only locked into screws on the left side of the plate (as shown in FIG. 12). This embodiment may be used in a one screw configured plate (not shown).

Figure 6:
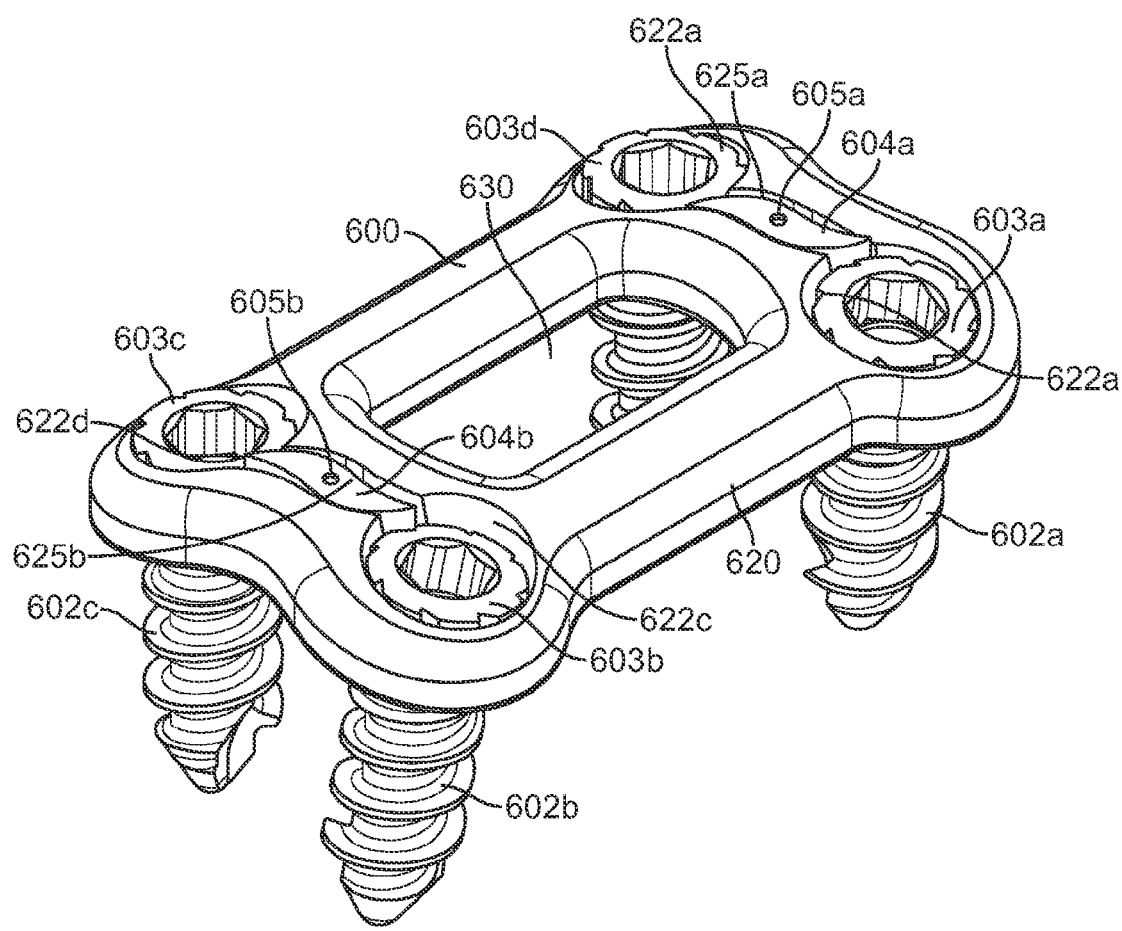

Referring to FIG. 6, bone screws are machined with "hook" shape notches in a circular pattern around the top face of the head (as shown in FIGS. 8 and 9). An "S" shaped recess 625 is cut out of the bone plate horizontally between the two bone screw holes 622. A threaded small diameter hole is drilled in the recess, centered horizontally and vertically between the bone screw holes. An "S" shaped tooth 604 (as shown in FIG. 10) is placed in the corresponding recess 625 and held in place with a small hex screw 1100 (as shown in FIG. 11). As the bone screw is tightened (clockwise rotation), the convex side of the "S" shaped tooth contacts the bone screw moving it into the recess of the plate. The "S" shaped tooth does not restrict tightening the bone screw. Once the bone screws are tightened, the concave side of the "S" shaped tooth locks into the "hook" shape notches in the head of the bone screw preventing the bone screw from rotating counter-clockwise or backing out. The "S" shaped tooth is locked into place via a small hex screw. In other embodiments, the "S" shaped tooth may be bias against the screw, with a spring or other means, and have a ratchet type engagement with the screw during tightening.

Referring to FIG. 6, the lumbar plate 600 includes a housing 620 having an interior opening 630 and screw openings 622(a, b, c, d) configured to be disposed symmetrically about the opening 630. In some embodiments, the lumbar plate 600 can include a plurality of interior openings or no interior openings at all. The screw openings 622 are configured to receive respective screws 602(a, b, c, d). In some embodiments, the lumbar plate 600 can accommodate placement of more than four screws (as illustrated in FIG. 6) or less than four screws, and may have differing number of screws at each body. Further, the screws 602 can have various lengths, widths, shapes, or any other characteristics.

In some embodiments, the shape of the housing 620 of the lumbar plate 600 can be rectangular, whereby the screw openings 622 are configured to protrude away from the housing 620, as shown in FIG. 6. In some embodiments, the shape of the housing 620 can be square, circular, oval, polygonal, or any other desired shape. Further, the housing 620 has an arcuate shape, wherein, upon insertion of the screws 602, axis of the screws 602 are configured to converge toward each other (for example, the axis of the screw 602a is configured to be convergent with the axis of the screw 602b; similarly for screws 602c and 602d). In some embodiments, the axis of all or some of the screws 602 are configured to converge toward each other, upon being inserted into the screw openings 622. Such arrangement allows angular placement of the lumbar plate 600 on a vertebral body or any other bone in the body. As can be understood by one skilled in the art, the arcuation of the housing 620 of the lumbar plate 600 can have any angle (including 0 degrees (or 180 degrees), which would correspond to a flat lumbar plate 600). In some embodiments, the axis of all or some of the screws are configured to be parallel or converge away each other. In some embodiments, the screw openings 622 can be configured to be contained within the housing 620 and not protrude away from its outer perimeter.

The screw openings 622 can be configured to retain screws 602 in various ways. In some embodiments, the screw openings 622 are configured to have a larger diameter near their top surface and a smaller diameter near their bottom surface. The smaller diameter can be selected to prevent screw 602 from falling through the opening 622 upon insertion of the screw 602. Hence, the smaller diameter can be smaller than the head portion of the screw 602. In some embodiments, the screw openings 622 can include screw retaining ledges (not shown) that are configured to protrude toward the center of the screw opening 622 and thereby, create a smaller diameter opening disposed in the screw opening 622. Such smaller diameter opening prevents screw 602 from falling through the opening 622 upon insertion. As can be understood by one skilled in the art, there are other ways of preventing screws 602 from falling through the openings 622. As can be understood by one skilled in the art, the openings 622 can have any desired shape, e.g., round, square, rectangular, polygonal, etc.

An exemplary screw 602 is illustrated in FIGS. 8-9. Referring to FIG. 8, the screw 602 includes a top portion 802, a middle portion 810, and a tip portion 808. To place the screw into a bone, a user (or any medical professional) would place the tip portion 808 proximate to the bone, and upon application of an instrument to the top portion 802 exert an appropriate amount of force to drive (by rotating) the screw 602 into the bone. The middle portion 810 includes threading 806 that is configured to allow such driving in a circular motion. The top portion 802 further includes instrument retaining opening 804 that accommodates placement of tools and instruments for driving the screw into the bone. In some embodiments, the opening 804 can have a hexagonal arrangement that allows placement of specialized tooling that matches such arrangement. The top portion 802 of the screw 602 can have a smooth outside surface or, in the alternative, can have locking grooves or notches 821. The notches 821 are configured to interlock the screw 602 with the locking tooth 604 (shown in FIGS. 6 and 10) or the locking tooth 1200 (shown in FIGS. 12 and 13). The notches 821 are configured to be slanted, thus, creating a stopper for the locking tooth 604 or 1200, thereby, preventing rotation of the screw 602.

Referring again to FIG. 6, the housing 620 of the lumbar plate 600 further includes locking teeth 604(a, b). The locking teeth 604 are configured to be placed between screw openings 622 into their respective locking mechanism openings 625(a, b). The locking mechanism openings 625 are configured to connect screw openings 622. In some embodiments, the opening 625a is configured to connect screw openings 622a and 622b, and the opening 625b is configured to connect screw openings 622c and 622d. Referring to FIGS. 6-7 and 10-11, the locking tooth 604 is illustrated (FIG. 7) being placed into the opening 625b.

Referring to FIGS. 10-11, the locking tooth 604 is illustrated in further detail. The tooth 604 includes a body portion 1007 having two curved ends 1003 and 1005 on each side of the body 1007. In some embodiments, the body portion 1007 includes an opening 1009 that allows removable insertion of a hex-locking screw 1100 (shown in FIG. 11) (same as screw 605 shown in FIG. 6). The hex-locking screw 1100 is configured to secure the tooth 604 to the plate 600 inside the openings 625 and allow rotation of the tooth 604. Referring to FIG. 11, the hex locking screw 1100 includes a shaft portion 1102 having partial threads portion 1104 that secure the screw 1100 to the body portion 620 of the lumbar plate 600 and an unthreaded portion 1105 having a length that is approximately equal to the width of the tooth 604. The screw 1100 also includes a top portion 1106 that allows a user (or any other medical professional) to secure the screw to the plate 600 using an instrument (or a hand). Referring back to FIG. 10, the tooth 604 is configured to have smooth curving surfaces throughout, so that when the tooth 604 is placed into the opening 625, its smooth surfaces are configured to create an uninterrupted surface with the interior surface of the openings 622. As shown in FIG. 6, the tooth 604 is configured to create a smooth surface with two interior surfaces of screw openings 622, and thus, accommodate locking of two screws 602. In other words, the locking mechanism or tooth 604 is configured to rotate from a first configuration in which the tooth 604 creates an uninterrupted surface with the interior surface of the openings 622 allowing the screw to pass, to a second configuration in which the tooth 604 engages and locks the screw 602 in place.

Referring back to FIG. 6, the locking tooth 604 is placed into the opening 625 by aligning the curved tips 1003, 1005 with corresponding curved portions of the opening 625 and dropping the tooth 604 into the opening 625 (first configuration). The tooth 604 can be secured to the body 620 of the lumbar plate 600 after at least one screw 602 is placed into the screw openings 622 (as shown in FIG. 6). To secure the screws 602, the locking tooth 604 is rotated with the tips 1003, 1005 of the tooth 604 being rotated until the snap into the notches 821 disposed on the screws 602 (second configuration). Hence, the tips 1003, 1005 lock the screws 602 to the screw openings 622, thereby preventing screws 602 from falling out. In some embodiments, the screws 602 can be placed after the tooth 604 is secured to the body 620. In such case, the tooth 604 is secured using hex-locking screw 605 inside the opening 625 of the body 620, then the tooth 604 is rotated into an unlocked position (whereby the tips 1003 and 1005 form a smooth surface with the interior surfaces of corresponding screw openings 622) and screws 602 are inserted. To lock the screws, the tooth 604 is rotated until the tips 1003, 1005 are snapped into one of the notches 821 of the screws 602. To unlock the screws 602, the locking tooth 604 is rotated in an opposite direction, thereby releasing the screws 602 and allowing them to be removed. As stated above, the rotation of the locking tooth 604 can be accomplished using any number of tools (including hands). A locked lumbar plate 600 arrangement is illustrated in FIG. 6.

FIGS. 12-13 illustrate another exemplary embodiment of the present invention's locking tooth 1200. The locking tooth 1200 is configured to have a trapezoidal shape with locking tips 1303, 1305, where the tips are configured to interact with the notches 821 of the screws 602. The locking tips 1303, 1305 are configured to be disposed at the bottom of the trapezoid. The tooth 1200 further includes an opening 1209 that is configured to secure the tooth 1200 inside the opening 1227 of the body 1220 of the plate 1201. The tooth 1200 can be secured to the body 1220 using the hex-locking screw 1100 shown in FIG. 11. To lock the screws 602, the tooth 1200 can be lifted from the opening 1227 and rotated (in some embodiments, the tooth 1200 can remain secured to the body 1220 using the hex-locking screw, i.e., the tooth 1200 is not being removed). Then, the screws 602 are inserted and then the tooth 1200 is rotated in an opposite direction and re-inserted into the opening 1227, thereby locking the screws 602.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A lumbar plate assembly for use between at least two vertebral bodies, comprising,
    a lumbar plate having at least one opening for each vertebral body;
    a screw configured to secure the lumbar plate to the vertebral body through the at least one opening, the screw includes a plurality of notches disposed on a top portion of the screw;
    a rotatable locking mechanism proximate the at least one opening for each vertebral body having a trapezoidal shape and includes at least one locking tip configured to interact with the at least one notch of the screw, the rotatable locking mechanism configured to rotate from a first configuration to a second configuration, the first configuration allowing the screw to pass into the at least one opening and the second configuration engaging the screw to prevent withdrawal of the screw from the at least one opening; and
    a locking screw configured to secure the rotatable locking mechanism to the plate.

2. The assembly according to claim 1, wherein the lumbar plate includes a recessed portion configured to accommodate placement of the rotatable locking mechanism.

3. The assembly according to claim 1, wherein the lumbar plate includes two screw openings configured to accommodate placement of two screws.

4. The assembly according to claim 3, wherein the locking mechanism is configured to be positioned between the two openings and further configured to simultaneously secure at least two screws within the two openings upon rotating the locking mechanism to the second configuration.

5. The assembly according to claim 1, wherein the locking mechanism is rotatably secured within the recessed portion.

6. The assembly according to claim 1, wherein the lumbar plate includes four screw openings configured to accommodate placement of four screws.

7. The assembly according to claim 6, wherein the locking mechanism is configured to be disposed within a recessed portion between two openings of the four screw openings and further configured to simultaneously secure at least two screws of the four screws.

8. The assembly according to claim 1, wherein the lumbar plate is configured to secure screws having a diameter in the range of 5.0 mm to 8.0 mm.

9. The assembly according to claim 1, wherein the at least one notch comprises one of a slanted notch, a grooved notch, and a hook-shaped notch.

10. The assembly according to claim 1, further comprising a plurality of notches in a circular pattern around the top portion of the screw.

11. A plate assembly for use between at least two vertebral bodies, comprising,
   a plate having a pair of openings for each vertebral body;
   a pair of screws for each pair of openings, each screw configured to secure the lumbar plate to the vertebral body through each opening, each screw including a top portion with an instrument retaining opening and a plurality of notches disposed in a circular pattern around the top portion;
   a pair of rotatable locking mechanisms, each rotatable locking mechanism proximate one pair of openings and including a pair of locking tips configured to interact with the plurality of notches of the pair of screws, each rotatable locking mechanism configured to rotate from a first configuration to a second configuration, the first configuration allowing screw to pass into the pair of openings and the second configuration engaging the tips with the notches to prevent withdrawal of the screws from the pair of openings; and
   a pair of locking screws configured to secure the pair of rotatable locking mechanisms to the plate.

12. The assembly according to claim 11, wherein the plurality of notches comprises one of slanted notches, grooved notches, and hook-shaped notches.

13. The assembly according to claim 11, wherein each pair of rotatable locking mechanisms is disposed within recessed portions between each pair of openings and configured to simultaneously secure at least two screws.

14. The assembly according to claim 11, wherein each pair of locking tips engages notches on the pair of screws to prevent rotation of the screws in a direction that causes withdrawal from the pair of openings.

* * * * *